United States Patent [19]
Cecil et al.

[11] Patent Number: 5,293,313
[45] Date of Patent: Mar. 8, 1994

[54] REAL TIME PHYSICIAN VIEW BOX

[75] Inventors: Robert A. Cecil, Solon; John J. Barni, Mayfield Village; Lawrence R. McMillen, Richmond Heights, all of Ohio

[73] Assignee: Picker International, Inc., Highland Heights, Ohio

[21] Appl. No.: 616,987

[22] Filed: Nov. 21, 1990

[51] Int. Cl.⁵ ............................................. G06F 15/00
[52] U.S. Cl. .................... 364/413.22; 382/54; 340/723
[58] Field of Search ............... 364/413.22; 382/54, 382/41, 6; 395/139; 340/723

[56] References Cited

U.S. PATENT DOCUMENTS

| | | | |
|---|---|---|---|
| 4,398,540 | 8/1983 | Takemura et al. | 358/112 |
| 4,550,422 | 10/1985 | VanPelt et al. | 378/207 |
| 4,563,740 | 1/1986 | Blake et al. | 364/413.22 |
| 4,612,540 | 9/1986 | Pratt | 340/723 |
| 4,733,229 | 3/1988 | Whitehead | 340/747 |
| 4,734,769 | 3/1988 | Davis | 358/146 |
| 4,852,002 | 7/1989 | Klausy | 364/413.22 |
| 4,853,970 | 8/1989 | Ott et al. | 382/22 |
| 5,042,077 | 8/1991 | Burke | 364/413.22 |
| 5,086,392 | 2/1992 | Nakajima | 364/413.22 |
| 5,099,846 | 3/1992 | Hardy | 364/413.22 |
| 5,119,080 | 6/1992 | Kajimoto et al. | 340/723 |

*Primary Examiner*—Roy N. Envall, Jr.
*Assistant Examiner*—Laura Brutman
*Attorney, Agent, or Firm*—Fay, Sharpe, Beall, Fagan, Minnich & McKee

[57] ABSTRACT

A medical diagnostic imager (10) reconstructs (96) raw scan data into digital image representations which are stored in a mass storage memory (46) such as DRAM or disk. As the scanner reconstructs the series of images, each digital representation image is transferred to an image VRAM (100) into one of a plurality of selected image areas. A video monitor (24) displays the electronic image representations from the image VRAM in the selected pattern of images, e.g. a 4×3 grid of images. The digital image representations are transferred to the image VRAM and displayed on the video monitor as they are generated such that the monitor displays the previously generated images and the most recently generated image as it develops during the reconstruction process. The diagnosing physician selects (104) one of the images and selectively adjusts (110) the window and level of its gray scale. After each of the images has been independently designated and its gray scale independently adjusted, one or more of the adjusted electronic image representations are transferred to a film printer (32) which makes a hard copy film print of the selected image(s). A graphics control (122) and a keyboard (132) enter data into a graphics VRAM (120) and a text VRAM (130), respectively. The electronic diagnostic image, graphics, and text data are merged (138) such that the graphics and text are superimposed on selected portions of the displayed video images.

17 Claims, 5 Drawing Sheets

REAL TIME PHYSICIAN VIEW BOX

BACKGROUND OF THE INVENTION

The present invention relates to the display of diagnostic images. It finds particular application in conjunction with the display of real time CT images and will be described with reference thereto. However, it is to be appreciated that the invention will find application in conjunction with the display of other video images including video images from other medical diagnostic modalities.

Traditionally, a CT scanner generates digital images that are later retrieved and displayed on a CRT monitor. A CT operator controls the scanning process and reviews the images as they are generated. The CT operator monitors each image for quality control purposes. That is, the CT operator reviews the images to be sure that they are good quality pictures that are complete with balanced gray scale. If the images have notable quality defects, the operator adjusts the scan parameters for subsequent scans and rescans any areas corresponding to unacceptable images. In the past, a new image was generated every 20 to 25 seconds. During this time, the operator could bring up previously generated images for further review, gray scale enhancement, or other cosmetic adjustments.

Typically, the diagnosing physician views the images offline at some later time. The images, which are stored on disk, are retrieved and displayed in a physician viewing room. Film copies of physician designated images are often made for the patient records. In other instances, film copies of the generated images are made first and the physician reviews the film copies rather than video monitor displays.

This delay in presenting the images to the diagnosing physician can be detrimental, particularly in trauma cases. In some instances, the diagnosing physician will stand behind the operator and watch the images as they are generated. However, this procedure has proven relatively unsatisfactory for diagnostic purposes. Diagnosing physicians normally do not diagnose from a single image. Rather, physicians normally compare a plurality of images. The images may represent healthy and affected tissue. The healthy image could be from a CT slice displaced from but close to the affected area or could come from the patient's file. Commonly, a multiplicity of images representing the affected area and tissue surrounding it are reviewed.

The CT operator and the physician often have conflicting adjustments to the displayed CT image. The CT operator makes adjustments for a cosmetically good image with a full range of gray scale. For diagnostic purposes, it is sometimes convenient for the physician to make a radical adjustment in the gray scale to emphasize some feature of the affected area, possibly at the expense of destroying the diagnostic value of the other portions of the image. When the physician is only adjusting the display of an image recorded on disk, such adjustments are no problem. However, making such adjustments to images being reviewed in a quality control fashion could adversely affect the diagnostic value of the stored and subsequent images.

The present invention provides a new and improved physician viewing arrangement which overcomes the above-referenced problems and others.

SUMMARY OF THE INVENTION

In accordance with one aspect of the present invention, medical diagnostic images passing to a storage media are loaded into a portion of a video RAM. The video RAM is configured such that a plurality of images are stored in the video RAM and displayed concurrently on a video monitor. A window control means is provided for selectively designated one of the stored images. A gray scale control means selectively controls window and level, i.e. contrast and gray scale, of the designated image. In this manner, a physician can view images in real time as they are generated while concurrently adjusting previously generated images to improve their diagnostic value.

In accordance with another aspect of the present invention, at least one of a text and graphics overlay video memory is provided. The graphics or text video RAM is connected with an appropriate keyboard or operator control to enable the operator to add notes or markings to the displayed diagnostic images.

In accordance with another more limited aspect of the present invention, a film printer is provided for selectively printing the adjusted video images either as a unit or individually, with or without the overlaying graphics or text.

One advantage of the present invention is that it provides the diagnosing physician with immediate diagnostic information without interrupting a scanning procedure.

Another advantage of the present invention is that a plurality of images are displayed concurrently to facilitate comparative anatomical image review.

Another advantage of the present invention is that the video monitor display is of substantially the same format as film displays.

Another advantage of the present invention is that it facilitates rapid, concurrent image formatting for filming.

Another advantage of the present invention resides in improved work efficiency for CT operators. Particularly in high speed image reconstruction systems in which images are generated every few seconds, the operator can view the currently formed image for quality control purposes while adjusting a prior image.

Still further advantages of the present invention will become apparent to those of ordinary skill in the art upon reading and understanding the preceding detailed description.

BRIEF DESCRIPTION OF THE DRAWINGS

The invention may take form in various steps and arrangements of steps, and in various components and arrangements of components. The drawings are only for purposes of illustrating the preferred embodiment and are not to be construed as limiting the invention.

DETAILED DESCRIPTION OF THE PREFERRED EMBODIMENTS

Figure 1:
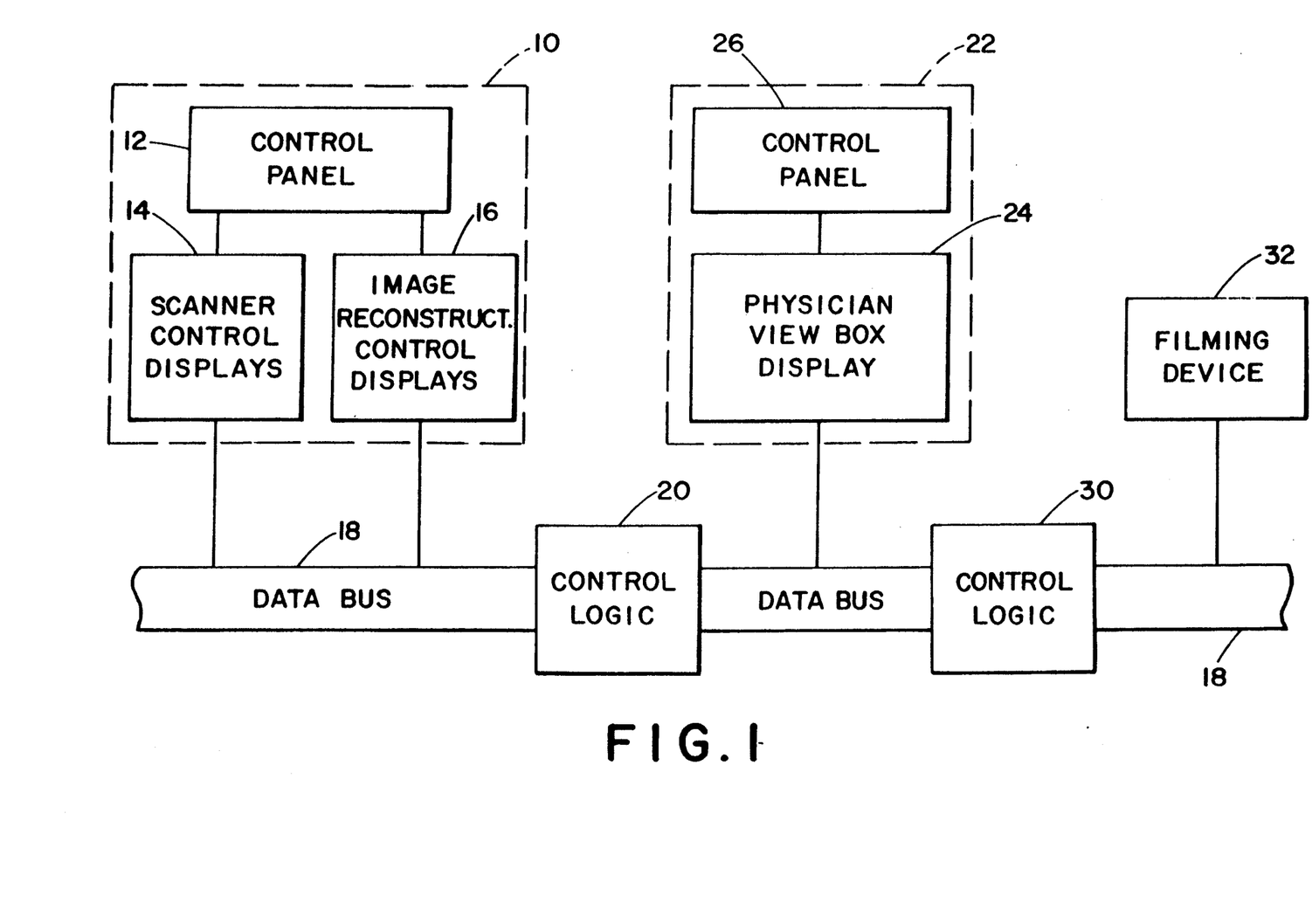
FIG. 1 is an overview of an image display and filming system in accordance with the present invention.

With reference to FIG. 1, a medical diagnostic scanner control system 10 such as a CT scanner, MR scanner, digital x-ray scanner, or the like includes an operator control panel 12. Associated control displays 14 enable the operator to set appropriate scan parameters for an optimal image. Image reconstruction control displays 16 facilitate control of the reconstruction of generated scan data into digital diagnostic image representations. The generated diagnostic images are conveyed in real time along a data bus 18.

A first or display control logic means 20 transfers completed images in real time to a physician view box means 22, independent of the scanning process. The view box means 22 includes a video monitor or other man-readable display 24 which displays a plurality of the generated images in a selectable array or pattern. An operator control panel or means 26 enables the physician or other operator to select various image display patterns, such as a 4×3 array of images, a 2×2 array, single image, etc. The operator control panel has controls for selecting and adjusting the window and level of each image independently, even while a currently generating image is accumulating in the next open image location of the array. The operator control panel also enables the physician to add diagnostic information to display images, such as descriptive text, circles, arrows, handwritten notations, and the like.

When the physician wants the displayed array of images or any one or more image of the array transferred to photographic film, a logic control means 30 transfers the appropriate image information to a filming device 32. The filming device automatically or semi-automatically produces a film or other hard copy image from the transferred video information.

Figure 2:
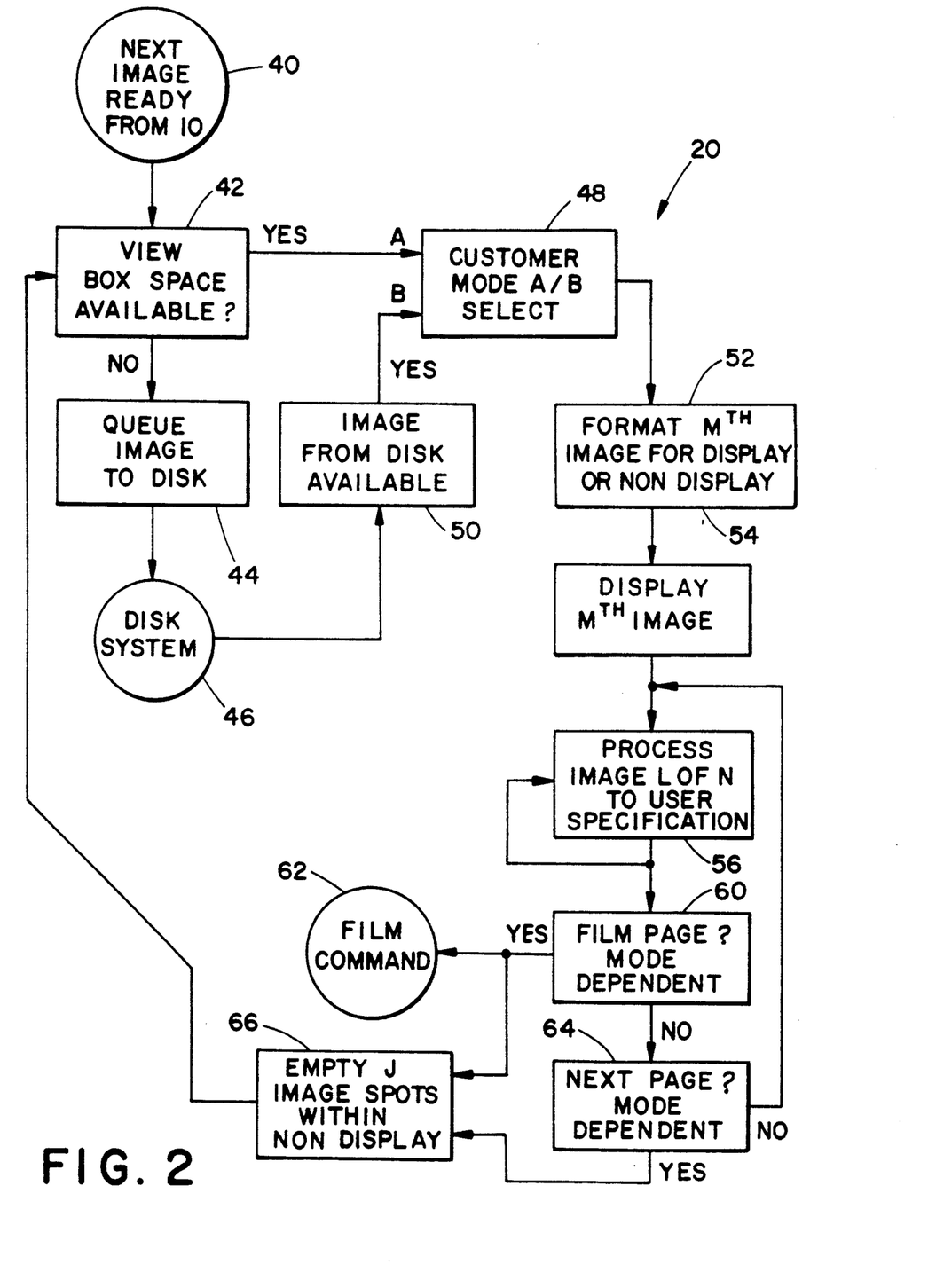
FIG. 2 is a programming flow chart illustrating the computer control functions of the first logic control means of FIG. 1.

With reference to FIG. 2, the logic control means zo has appropriate hardware and software for performing a step 40 of receiving a next electronic image representation from scanner means 10 A step or means 42 determines whether space is available to display another image on the view box display monitor 24. If view box space is unavailable, a step or means 44 queues the image to a disk memory 46. A mode selection means 4s in the control panel 26 allows the physician to select either images received in real time from the scanner 10 or retrieved by a step or means 50 from the disk memory.

A step or means 52 formats each imaqe received for display. A step or means 54 displays each received image sequentially in a preselected array pattern on the view box monitor 24. A processing step or means 56 processes each previously received image individually to user's specifications. The processing of the image may include changing the dynamic range or window, i.e. whether the imaged tissue varies in large or small steps between the white and black scale values. The image processing also includes selectively adjusting the number or linearity of the steps between the white and black gray scale levels.

A step or means 60 determines whether a film print is to be made. If a film print is to be made, a film command means 62 sends an appropriate film command to the second control logic means 30. If a film print is not to be made, a next page step or means 64 returns to the image processing step or means 58 and the next image is processed to the user's specifications, unless all the images on the display or page have not yet been adjusted. If all the images have been adjusted, a commencement of another matrix array of images on the monitor is commenced. A space available determining means or step 66 determines whether there are places available on the display screen to display another image. The availability of image space is communicated to the view box space available means or step 42.

Figure 3:
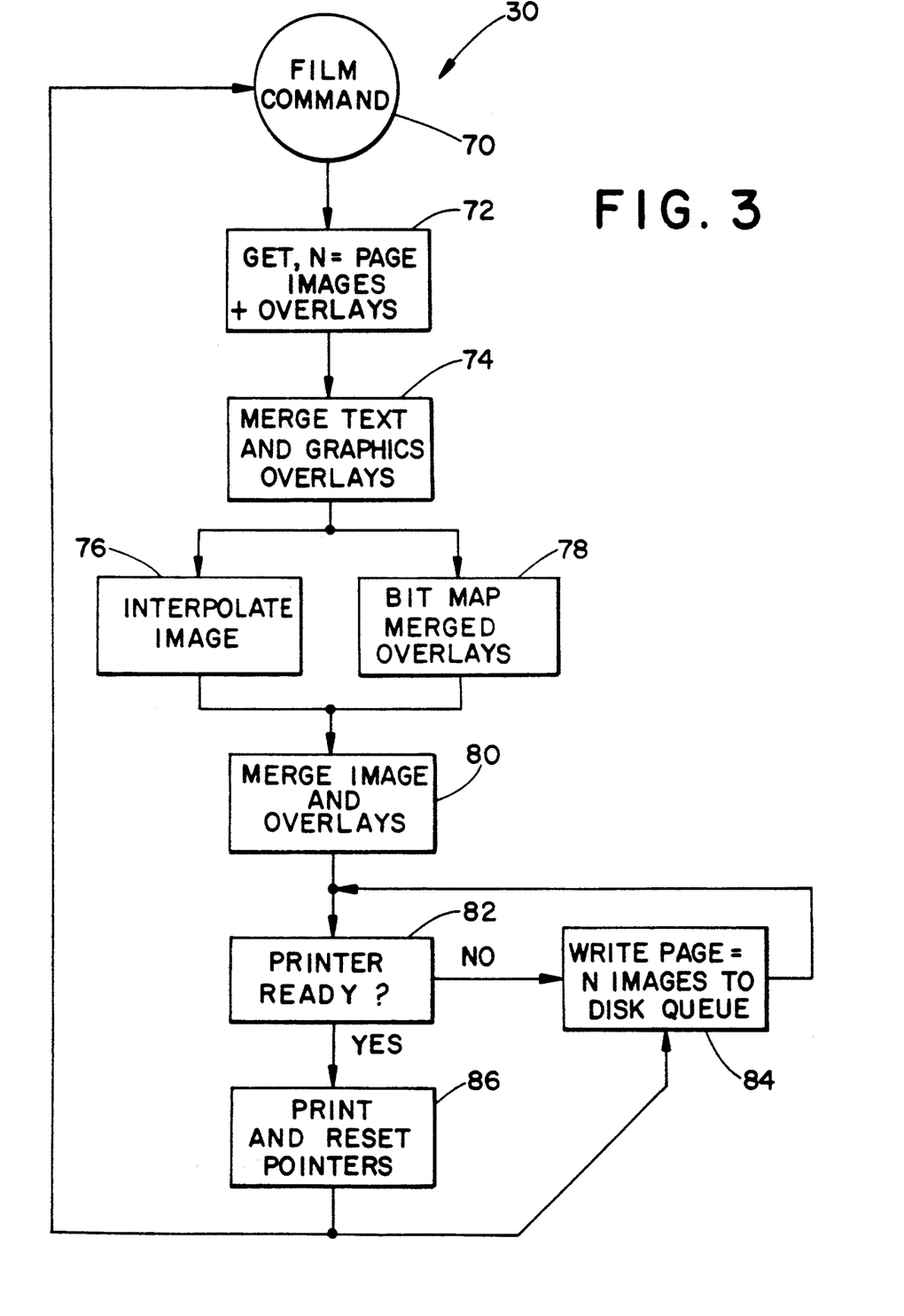
FIG. 3 is a programming flow chart illustrating the computer function of the second logic control of FIG. 1.

With reference to FIG. 3, the film command from step or means 62 of control logic means 20 is communicated from a film command receiving step or means 70 of the second logic control means 30. A step or means 72 retrieves the video images and overlay images transmitted along the data bus 16 from the physician's view box means 22. Again, the overlays are separate images which contain the text and graphics that were added to the images. A step or means 74 merges the text and graphic overlays. That is, a text video image display and a separate graphics image video display have the same coordinate system such that the two can be directly superimposed. The merging step or means combines the two image representations. An image interpolating means or step 76 expands the size of an image representation, where appropriate. That is, the filmed image may be a single one of the image representations or the complete matrix of image representations. The video image information is scaled up or down as may be appropriate to print only the selected portion. A bit map step or means 78 converts the text and graphic information into a bit map format. The text would normally be entered in a text font format and the graphics may be entered in either a bit map or a vector format. The bit map step or means converts this information into a bit map whose pixel values correspond with the pixel values of the interpolated image means 76.

Once the medical diagnostic image and the bit map are interpolated to have matching sizes so that they overlay precisely, a merging step or means so merges the bit map overlays and medical diagnostic image. A step or means 82 determines if the printer 32 is ready. If not, a step or means 84 transfers the merged print ready image to the disk 46 for storage until the printer is ready. If the printer is ready, a step or means 86 causes the printer to print the image and reset appropriate parameters. After the printing process is complete, the step or means returns to step or means 84 to retrieve any images which were stored on the disk awaiting printer availability. If no images are waiting on the disk to be printed, the step or means 86 returns to the film command receiving step or means 70.

Figure 4A:
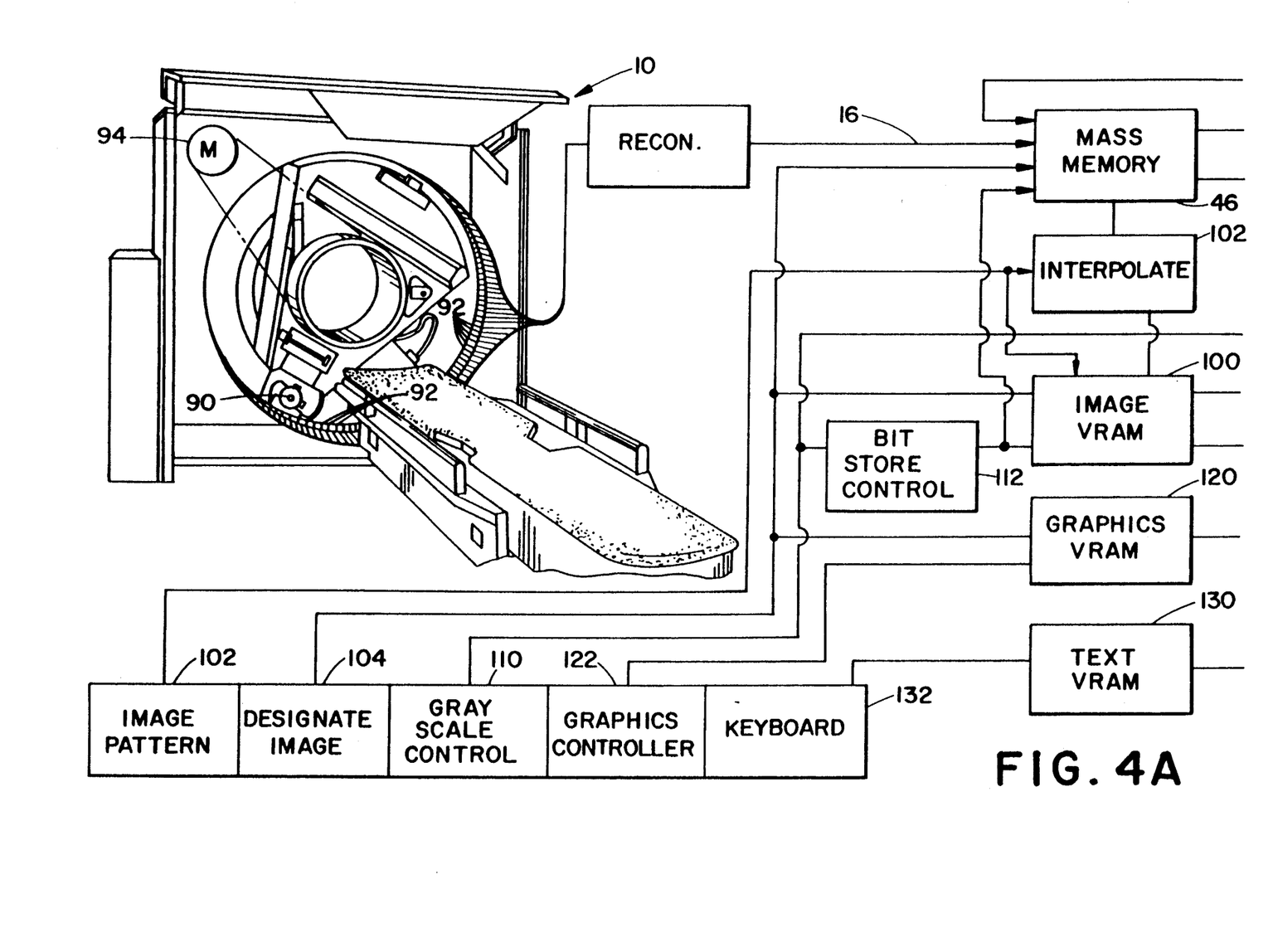
FIGS. 4A and 4B are a diagrammatic illustration of a CT scanner and associated hardware for implementing the present invention.
Figure 4B:
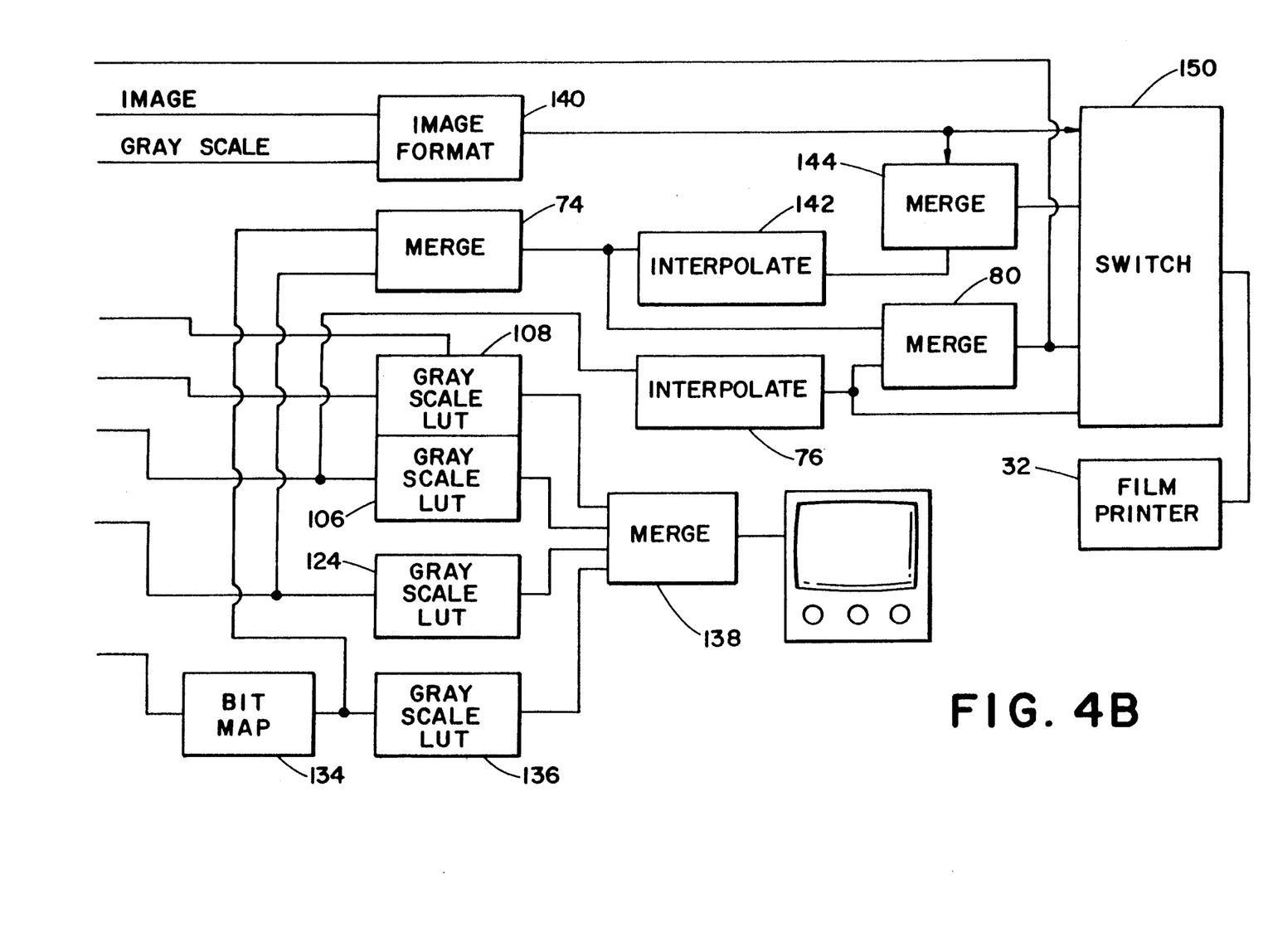

With reference to FIGS. 4A and 4B, the diagnostic imaging means 10 is illustrated as a CT scanner including a source of penetrating radiation 90 and an arc of radiation detectors 92 for receiving radiation that has traversed an imaged slice of a patient. A rotating means 94 causes the source of x-rays to rotate around the imaged slice. An image reconstruction means 96 reconstructs digital electronic diagnostic image representations from the radiation attenuation data collected by the radiation detectors 92. Each reconstructed digital electronic image representation is communicated to the disk or other mass storage means 46. In the preferred embodiment, each image is 512 pixels by 512 pixels, each pixel having 12 bits of gray scale resolution.

An image video random access memory (VRAM) 100 is formatted to receive images in a selected matrix array or pattern by an operator controlled means 102. The operator designates the number of images to be displayed on the video monitor 24, e.g. twelve images. In the preferred embodiment, the video monitor 24 has about 1024×1024 display pixels and displays one of about 256 gray scales between White and full black at each pixel, i.e. eight bits of gray scale resolution per pixel. The image video memory 100 also has about 1024×1024×8 memory elements for static display plus additional memory described below for the adjusting procedure. As each image is reconstructed and sent to the memory 46, it is forwarded to the next available image region of the image memory 100. If more than four images are to be displayed, an interpolating means 102 averages pixel values to reduce the size of the image.

A window control or image selection means 104 moves a curser along the display on the video monitor 24 to enable the diagnosing physician to designate one of the displayed images for adjustment. The window control likewise denotes the corresponding storage regions of the mass memory 46 and the video memory 100. The window control causes the full twelve bits of gray scale information corresponding to each pixel of the designated image to be transferred into the denoted storage regions video memory and a 512×512×4 supplemental storage area for adjustment. The supplemental storage area is formatted such that the designated image appears to be stored in an M×N×12 memory area, where M and N are the dimensions of the image in the selected array or pattern.

A first qray scale look up table means 106 converts the digital gray scale information from the non-designated images in the image video memory 110 into appropriate analog gray scale information for the video monitor 24. A second or active qray scale look up table 108 converts gray scale information from the image designated by the window control means 104 into the appropriate gray scale levels for display on the video monitor. A gray scale control means 110 selectively controls the active image gray scale look up table 108 to adjust which n, eight in the preferred embodiment of the m, twelve in the preferred embodiment, are utilized to designate the displayed gray scale. Note that to display the eight least significant bits gives very fine gray scale gradations between steps but has a relatively limited range of radiation absorption values between white and black. Analogously, displaying the eight most significant bits displays the full range of radiation absorption information available but has relatively large steps between gray scale values and loses the least significant bits of gray scale information. When the examining physician has adjusted which gray scale bits are displayed, i.e. the window and level values, a bit storage control means 112 causes the selected m, eight in the preferred embodiment, bits to be stored in the video memory, 100 and the remaining n−m, four in the preferred embodiment, bits to be discarded. The window control means 104 moves the curser to the next image and an analogous adjustment process is repeated.

A graphics video memory, particularly a VRAM 120 has 1024×1024 pixel values to store graphics information. The graphics VRAM need only have a single bit of depth per pixel if the graphics are only to be displayed in black or white. If intermediate gray scales or colors are to be provided, additional bits of resolution are required corresponding to each pixel. A graphics control means 122 is operated by the diaqnosing physician to cause selected pixels or regions to be displayed as black or white. For example, the physician might draw a circle around a region of interest of a slice, write a note, or the like. A gray scale look up table means 124 converts the digital output of the graphics VRAM into appropriate analog values for display on the video monitor 24. The graphics VRAM also receives control signals from the video control means 104 to produce the curser display.

A text VRAM 130 stores descriptive text information entered from a keyboard 132. The text may provide titles below or between various pictures, may include diagnostic information overlaying an image or designated positions of the array. For example, eleven pictures could be displayed and a full page of text typed into the twelfth position. If the text information is stored in font format, a bit map means 134 converts the text information from font to bit map format. A gray scale look up table 136 converts the digital bit map information into appropriate analog information for display on the video monitor 24. A merging means 138 merges the analog output of the gray scale look up tables in order to superimpose the image, graphics, and text displays. In this manner, the image, graphics, and text displays appear superimposed on the video monitor yet each can be altered, revised, or corrected without affecting the information stored in the others.

When the diagnosing physician decides to print all or part the array of images displayed on the video monitor 24, the information from the VRAMS 100, 120, and 130 is transferred to the film printer 32. Specifically, a merging means 74 merges the digital text and graphics information. The interpolating means 76 interpolates the diagnostic image video information as necessary, and the merging means 80 merges the diagnostic image, graphics, and text digital data.

If a single one of the displayed images is to be filmed and if the image was reduced as it was transferred into the image VRAM 100, then the same image information is withdrawn from the memory 46 by an image formatting means 140. An indication of Which bits of gray scale were selected by the physician is also withdrawn from the memory 46 such that the image formatting means 14c formats the image with the appropriate gray scale levels. An interpolating means 142 identifies and enlarges the graphic and text data, if any, which overlays the selected image. A merging means 144 merges the diagnostic image, graphic, and text information.

A switching means 150 under operator control selectively connects one of the digital image data from memory 46, the digital image data from memory 46 with superimposed text or graphics, the superimposed digital image text, and graphics information from the video memories, or the diagnostic image without superimposed text or graphics from the video image memory 100 for connection with the film printer 32.

The invention has been described with reference to the preferred embodiments. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiments, the invention is now clained to be:

1. A diagnostic image display system comprising:
    a diagnostic scanner which generates a series of high gray scale resolution digital electronic diagnostic image representations;

a digital mass storage means for receiving and storing at least the series of generated digital high gray scale resolution electronic image representations;

an interpolating means for reducing a number of pixels per digital high gray scale resolution electronic image representation received from the mass storage means to generate a plurality of reduced pixel digital electronic image representations;

a digital image video memory means formatted to store a plurality of the reduced pixel digital electronic image representations for concurrent display in a common video frame in a selected array pattern;

a bit storage control for independently controlling a fraction of gray scale resolution bits of each reduced pixel electronic image representation stored in the digital image video memory means, such that each stored reduced pixel digital electronic image representation has only an independently selected fraction of the gray scale resolution bits received from the digital mass storage means;

a video monitor means connected with the digital image video memory means for converting the digital electronic image representations stored in the digital image video memory means into a common analog video frame signal for display of human-readable images in the selected pattern, the fraction of gray scale resolution bits of each displayed image representation of the common video frame being independently controlled.

2. The system as set forth in claim 1 further including:

a text video memory means for storing text data;

a text control means for inputting text data into the text memory means;

digital to analog converting means for converting digital image and text data from the image and text memory means into analog video values;

a merging means for merging the text and image video values, the merging means supplying the merged analog video values to the video monitor such that the text is displayed on the image, whereby the text can be changed and revised without affecting the image representations.

3. A diagnostic image display system comprising:

a diagnostic scanner which generates a series of digital electronic diagnostic image representations, each reconstructed image representation having n bits of gray scale for each pixel;

a mass storage means for receiving and storing at least the series of generated electronic image representations with n bits of gray scale;

a diagnostic image video memory means formatted to store a plurality of electronic image representations with m bits of gray scale for concurrent display as a single image in a selected array pattern in which each of the image representations has reduced physical dimensions, the image video memory means stores precedingly received digital image representations and receives and stores newly generated image representations;

a windowing means for independently selecting which m of the n bits of gray scale for each image representation stored in the mass storage mean are stored in the image video memory means for display, where m and n are integers and m is less than n such that the windowing means selects only a fraction of available gray scale information independently for each image representation;

a video monitor connected with the windowing means for converting the fraction of the gray scale information of each electronic image representation passed from the image video memory means into a common human-readable display having m bits of gray scale.

4. The system as set forth in claim 3 wherein the windowing means for selecting m bits for display includes:

a first gray scale conversion means for selectably converting m of the n bits per pixel of the selected image into corresponding analog gray scale values;

a means for selectively adjusting which m of the n bits of the selected image are converted by the first gray scale conversion means;

a bit storage control means for controlling the image video memory means to store the m selected bits of each selected image after adjustment.

5. The system as set forth in claim 4 wherein non-selected images have m bits per pixel stored in the image video memory and further including a second gray scale conversion means for converting the m bits per pixel into corresponding gray scale values for display on the video monitor.

6. The system as set forth in claim 3 further including a film printer means operatively connected with the image video memory means for producing a film image from digital data read from the image video memory means.

7. A diagnostic image display system comprising:

an image video memory means for storing a plurality of digital image representations for concurrent display in a common video picture each image representation being composed of digital pixel values corresponding to an array of pixels of a displayed image;

a windowing means for independently adjusting which fraction of bits of the digital pixel values gray scale characteristics of each image representation are stored in the image video memory means without adjusting a preselected fraction of the bits of the pixel values of other image representations of the common video picture;

a graphics video memory means for storing a corresponding number of pixels of digital data as the image video memory means;

a graphic control means for inputting graphic display data into the graphic video memory means;

a digital to analog converting means for converting digital image representations and graphics data from the image video memory means and graphics video memory means into analog video values;

a merging means for merging the analog graphics and image video values, the merging means supplying the merged analog video values to a video monitor such that the graphics are displayed superimposed on the image representations in the common vide picture, whereby the graphics can be changed and revised without affecting the image representations.

8. The system as set forth in claim 7 further including:

a means for merging digital image and graphics data read from the image and graphics video memory means;

a film printer means for converting the merged digital image and graphic values into a film print.

9. A method of displaying diagnostic images, the method comprising:

receiving a series of electronic digital diagnostic image representations, each image representation including an array of gray scale pixel values;

storing the electronic image representation gray scale values;

selecting an image display pattern for displaying a plurality of the stored image representations each in one of a plurality of image display areas of a single video picture;

as each electronic image representation is received, converting the electronic image representation into a human-readable image displayed in a next image display area of the single video picture;

designating a one of the displayed human-readable images in one of the image display areas of the single video picture;

selectively adjusting stored gray scale values of only the designated image without adjusting the gray scale values of the single video picture as a whole, while displaying concurrently in the single video picture (i) the designated image as its gray scale values are adjusted and (ii) non-designated images each with its respective stored gray scale values.

10. The method as set forth in claim 9 wherein the electronic image representations are generated by a diagnostic scanner in which images are developed as additional data is received, whereby the displayed image converted from the most recently received electronic image representations develops as gray scale adjustments are made to precedingly received electronic image representation gray scale values.

11. The method as set forth in claim 10 further including transferring at least one of the adjusted electronic image representations to a printing means for making a hard copy print of the image.

12. The method as set forth in claim 10 further including storing at least one of graphics and text electronic information and converting the at least one of the graphics and text electronic information into a man-readable display superimposed on at least one of the displayed images.

13. The method as set forth in claim 12 further including transferring at least one of the adjusted electronic image representations and the at least one of the graphics and text electronic information to a printing means for making a hard copy print of the image with at least one of the graphics and text superimposed on the image.

14. A method of independently adjusting window and level of each of a plurality of concurrently displayed images, the method comprising:

receiving a series of electronic digital diagnostic image representations, each image representation including an array of gray scale pixel values, the gray scale values for each pixel being depicted by a first plurality of bits;

storing the electronic image representation gray scale values of each of a plurality of the received image representations;

selecting an image display pattern for displaying the plurality of the image representations each in one of a plurality of image display areas;

as each electronic image representation is received, converting the received electronic image representation into a human-readable image in a next image display area;

designating a one of the displayed human-readable images in one of the image display areas;

independently adjusting a gray scale window and a level of the gray scale pixel values of the designated digital electronic image representation without adjusting gray scale pixel values of non-designated digital electronic image representations while displaying (i) the non-designated images and (ii) the designated image with the adjusted gray scale window and level.

15. A diagnostic image display system comprising:

a digital mass memory means for receiving and storing a series of digital electronic image representations from a digital image representation source means including an image reconstruction means of a diagnostic scanner, the image reconstruction means supplying digital image data which is stored in the digital mass memory means as an image is reconstructed to develop a completed electronic image representation;

a digital video memory means which receives and stores in digital format a single video image which is a composite of a plurality of electronic image representations in a selected pattern;

a gray scale adjusting means for independently adjusting digital gray scale values of each of the image representations of the single video image stored in the video memory means;

a video monitor connected with the video memory means for converting the single video image stored therein into a man-readable display.

16. The system as set forth in claim 15 further including:

an overlay memory means for storing at least one of graphic and text electronic information;

a merging means for selectively merging the single video image from the video memory means with the electronics information from the overlay memory means such that the at least one of the graphics and text is superimposed on the displayed single video image.

17. The system as set forth in claim 16 further including a film print means for converting single video image and graphic and text information into a hard copy print.

* * * * *